US012805837B2

(12) United States Patent
Iwaki et al.

(10) Patent No.: US 12,805,837 B2
(45) Date of Patent: Nov. 24, 2026

(54) CART FOR ULTRASOUND APPARATUS HAVING CASTER WITH PEDESTAL CONNECTING TWO SIDE BEAMS FOR ACCOMMODATING BATTERIES AND WEIGHT BALANCE

(71) Applicant: FUJIFILM Corporation, Tokyo (JP)

(72) Inventors: Takuro Iwaki, Tokyo (JP); Ryosuke Ogura, Tokyo (JP); Tomoki Inoue, Tokyo (JP); Kengo Katagiri, Tokyo (JP); Takayoshi Saito, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 19/059,237

(22) Filed: Feb. 20, 2025

(65) Prior Publication Data

US 2025/0295383 A1 Sep. 25, 2025

(30) Foreign Application Priority Data

Mar. 19, 2024 (JP) ................................ 2024-043901

(51) Int. Cl.
*A61B 8/00* (2006.01)
*B62B 3/10* (2006.01)

(52) U.S. Cl.
CPC .............. *A61B 8/4405* (2013.01); *A61B 8/56* (2013.01); *B62B 3/10* (2013.01); *B62B 2202/56* (2013.01)

(58) Field of Classification Search
CPC ....... A61B 8/4405; A61B 8/56; A61B 8/4411; A61B 8/4427; A61B 8/44; A61B 50/13;
(Continued)

(56) References Cited

U.S. PATENT DOCUMENTS

2013/0330588 A1* 12/2013 Ahn .................... A61B 8/4427 600/443
2014/0350357 A1* 11/2014 Lee ..................... A61B 8/4405 600/443

(Continued)

FOREIGN PATENT DOCUMENTS

JP 2017-086325 A 5/2017
JP 2023-070380 A 5/2023
WO 2007/013084 A1 2/2007

OTHER PUBLICATIONS

The extended European search report issued by the European Patent Office on Jul. 28, 2025, which corresponds to European Patent Application No. 25163070.3-1122 and is related to U.S. Appl. No. 19/059,237.

*Primary Examiner* — Serkan Akar
(74) *Attorney, Agent, or Firm* — Studebaker Brackett PLLC

(57) ABSTRACT

A cart includes a caster unit, a support, a mounting part, and a connector. The caster unit includes a total of four wheels, that is, casters provided on front, rear, left, and right sides. A lower end of the support is attached to the caster unit and the support extends upward. The support is disposed on a rear side of a center of the caster unit in a front-rear direction. The mounting part is attached to an upper end of the support, and an ultrasound diagnostic apparatus is mounted on the mounting part. A battery unit that supplies power to the ultrasound diagnostic apparatus and is disposed in front of the support is connected to the connector.

14 Claims, 7 Drawing Sheets

(58) Field of Classification Search
CPC .............. A61B 2560/0214; B62B 3/10; B62B 2202/56; B62B 3/00; B62B 5/00; Y02E 60/10
See application file for complete search history.

(56) References Cited

U.S. PATENT DOCUMENTS

| | | | | |
|---|---|---|---|---|
| 2020/0008990 | A1 | 1/2020 | Harrison | |
| 2022/0149448 | A1* | 5/2022 | He | H01M 10/46 |
| 2023/0148030 | A1 | 5/2023 | Chihara et al. | |

* cited by examiner

CART FOR ULTRASOUND APPARATUS HAVING CASTER WITH PEDESTAL CONNECTING TWO SIDE BEAMS FOR ACCOMMODATING BATTERIES AND WEIGHT BALANCE

CROSS-REFERENCE TO RELATED APPLICATIONS

The present application claims priority under 35 U.S.C. § 119 to Japanese Patent Application No., 2024-043901 filed on Mar. 19, 2024. The above application is hereby expressly incorporated by reference, in its entirety, into the present application.

BACKGROUND

1. Technical Field

A technique of the present disclosure relates to a cart for a medical apparatus.

2. Description of the Related Art

A cart for a medical apparatus on which a medical apparatus is mounted is used in a medical field. The cart for a medical apparatus is useful in a case where a doctor makes a round to give medical care while moving between a plurality of patients, and the like. The cart for a medical apparatus includes, for example, a caster unit that includes a total of four wheels, that is, casters provided on front, rear, left, and right sides, a support of which a lower end is attached to the caster unit and which extends upward, and a mounting part which is attached to an upper end of the support and on which the medical apparatus is mounted. Further, a battery unit that supplies power to the medical apparatus is attached to the cart.

JP2023-070380A and JP2017-086325A disclose carts for a medical apparatus in which a lower end of a support is attached substantially at the center of a caster unit in a front-rear direction and a left-right direction. In the cart for a medical apparatus disclosed in JP2023-070380A, a battery is attached to a body part of an ultrasound diagnostic apparatus as a medical apparatus. The body part is disposed on the rear side of the support on a pedestal of the caster unit.

In the cart for a medical apparatus disclosed in JP2017-086325A, a battery is attached to a battery box body part including a power converter that converts direct current power supplied from the battery into alternating current power for a commercial power source, an electric outlet that supplies the alternating current power to a medical apparatus, and the like. Further, the battery box body part is disposed on the rear side of the support on a pedestal of the caster unit (see a third embodiment of JP2017-086325A).

SUMMARY

A medical apparatus having a certain weight (for example, several kg) is mounted on a mounting part. For this reason, considering weight balance, it is preferable that the attachment position of the support is present substantially at the center of the caster unit in the front-rear direction and the left-right direction as disclosed in JP2023-070380A and JP2017-086325A. However, in a case where the support is present substantially at the center of the caster unit in the front-rear direction and the left-right direction, the legs of the user bump into the support, which makes it difficult to perform work. Therefore, a configuration in which weight balance is easily ensured and workability of a user can be improved has been desired.

One embodiment of the technique of the present disclosure provides a cart for a medical apparatus in which weight balance is easily ensured and workability of a user can be improved.

A cart for a medical apparatus according to an aspect of the present disclosure comprises: a caster unit that includes a plurality of casters provided on front, rear, left, and right sides; a support of which a lower end is attached to the caster unit and which extends upward and is disposed on a rear side of a center of the caster unit in a front-rear direction; a mounting part which is attached to an upper end of the support and on which a medical apparatus is mounted; and a connector to which a battery unit that supplies power to the medical apparatus and is disposed in front of the support is connected.

It is preferable that the caster unit includes two side beams to which the front and rear casters are attached and which extend in the front-rear direction, and the battery unit is disposed between the two side beams in a state in which the battery unit is connected to the connector.

It is preferable that the side beam is provided with a holding mechanism that holds the battery unit to allow the battery unit to be attachable and detachable.

It is preferable that the holding mechanism includes a guide rail that guides the battery unit, which is to be slid from a front side, toward the connector.

It is preferable that, in a state in which the battery unit is connected to the connector, an outer peripheral surface of the battery unit and outer peripheral surfaces of the side beams on which the outer peripheral surface of the battery unit borders form one smooth surface.

It is preferable that the caster unit further includes a pedestal that connects the two side beams, the pedestal is disposed on a rear side of a center of the caster unit in the front-rear direction, and a lower end of the support is attached to the pedestal.

It is preferable that the pedestal is provided with the connector, and the battery unit is disposed between the two side beams and the pedestal in a state in which the battery unit is connected to the connector.

It is preferable that a rear end portion of the pedestal is positioned in front of rear end portions of the side beams.

It is preferable that shapes of cross sections of the battery unit and the pedestal orthogonal to the front-rear direction are the same.

It is preferable that the battery unit protrudes above and below the side beams as viewed from a front side in a state in which the battery unit is connected to the connector.

It is preferable that a centroid of the battery unit is positioned at a level equal to or lower than an upper surface of the side beam in an up-down direction as viewed from the front side in a state in which the battery unit is connected to the connector.

It is preferable that a centroid of the battery unit is positioned between an upper surface and a lower surface of the side beam in an up-down direction as viewed from the front side in a state in which the battery unit is connected to the connector.

It is preferable that both left and right side surfaces of a portion of the battery unit, which protrudes below the side beams in a state in which the battery unit is connected to the connector, are inclined toward sides opposite to the casters as viewed from the front side.

It is preferable that a contour of the mounting part is positioned within a contour of the caster unit as viewed from above.

It is preferable that the battery unit is for additional installation.

It is preferable that a plurality of types of the battery units having different capacities and sizes are capable of being connected to the connector.

It is preferable that the medical apparatus is an ultrasound diagnostic apparatus.

According to the technique of the present disclosure, it is possible to provide a cart for a medical apparatus in which weight balance is easily ensured and workability of a user can be improved.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
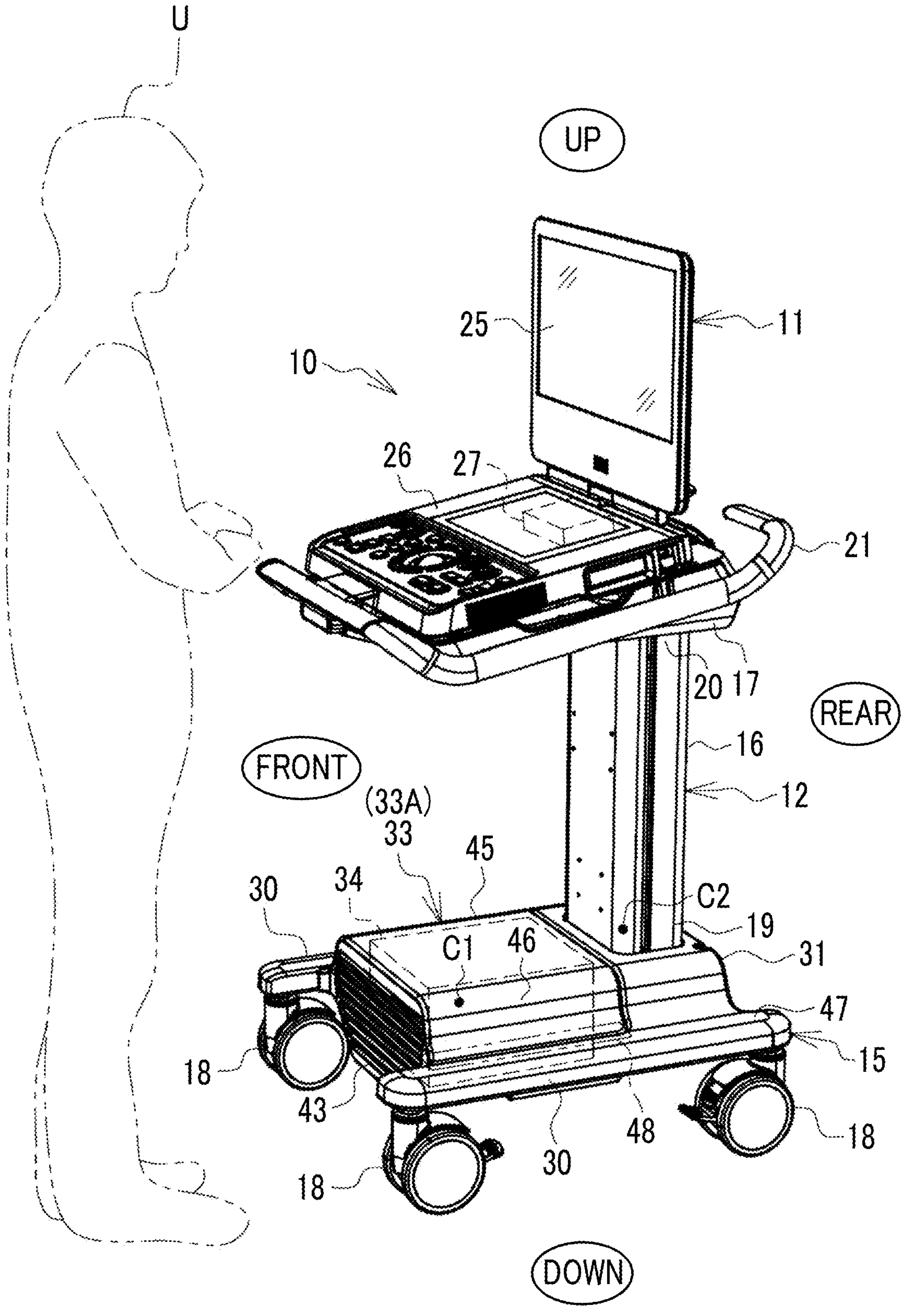
FIG. 1 is a perspective view showing an ultrasound diagnostic system in a state in which a battery unit is attached to a cart for an ultrasound diagnostic apparatus.
Figure 2:
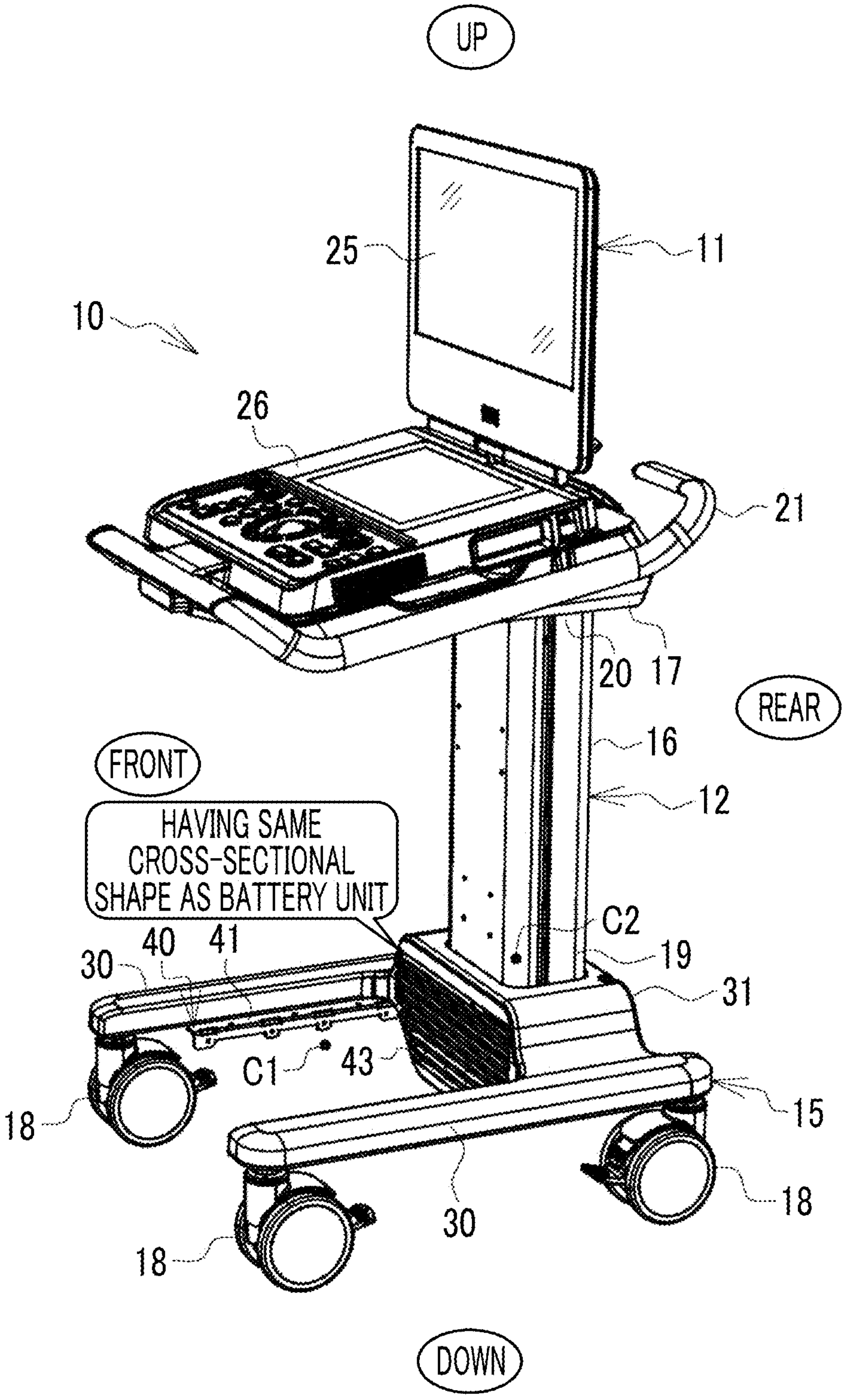
FIG. 2 is a perspective view showing the ultrasound diagnostic system in a state in which the battery unit is detached from the cart for the ultrasound diagnostic apparatus.
Figure 3:
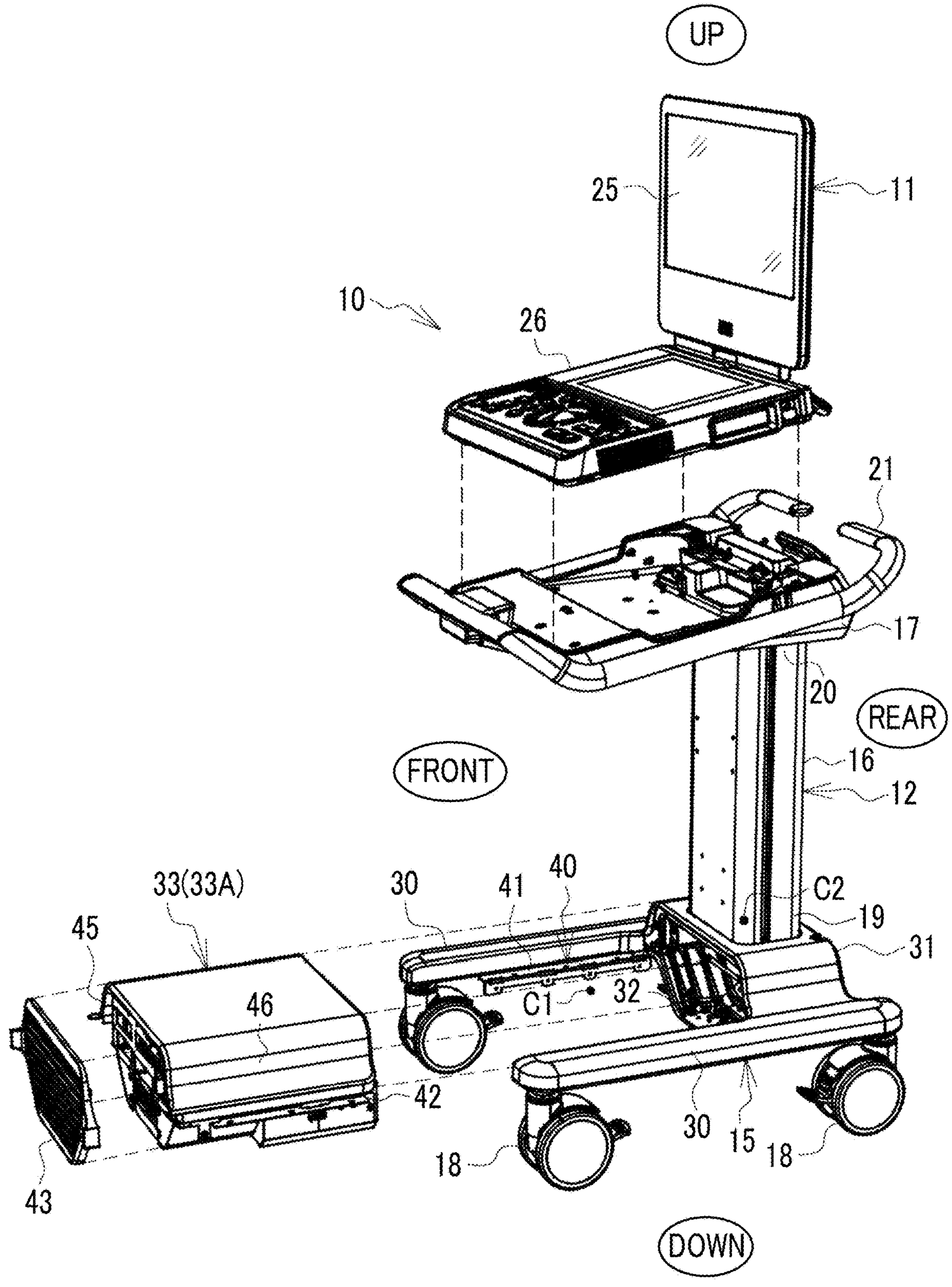
FIG. 3 is an exploded perspective view of the ultrasound diagnostic system.

For example, as shown in FIGS. 1, 2, and 3, an ultrasound diagnostic system 10 includes an ultrasound diagnostic apparatus 11 and a cart for the ultrasound diagnostic apparatus (hereinafter, simply referred to as a cart) 12. The cart 12 is literally a cart dedicated to the ultrasound diagnostic apparatus 11, and comprises a caster unit 15, a support 16, a mounting part 17, and the like. The ultrasound diagnostic apparatus 11 is an example of a "medical apparatus" according to the technique of the present disclosure. Further, the cart 12 is an example of a "cart for the medical apparatus" according to the technique of the present disclosure.

The caster unit 15 is disposed on a lower side (floor surface side). The caster unit 15 includes a total of four wheels, that is, casters 18 provided on the front, rear, left, and right sides. The casters 18 are disposed at four vertices of a rectangle that is formed of two long sides parallel to a front-rear direction and two short sides parallel to a left-right direction. Each of the casters 18 rotates about an axis parallel to an up-down direction by an angle of 360°. The casters 18 allow the cart 12 to move in a medical facility. Here, the term "front" or "front side" is a side to which a user U has access in a case where the user is to operate the ultrasound diagnostic apparatus 11. The term "rear" or "rear side" is a side opposite to the side to which the user U has access in a case where the user is to operate the ultrasound diagnostic apparatus 11. The term "left and right" refers to left and right as viewed from the "front" or the "front side". Further, the term "up and down", "upper side" or "lower side" means up and down in a vertical direction. Furthermore, the term "parallel" mentioned here refers to not only "completely parallel" but also "parallel" in the sense of including an error that is generally allowed in a technical field to which the technique of the present disclosure belongs and that does not contradict the gist of the technique of the present disclosure.

The support 16 has the shape of a substantially quadrangular prism, and a lower end 19 thereof is attached to the caster unit 15. The support 16 extends upward from the lower end 19, and an upper end 20 thereof is attached to the mounting part 17. The support 16 and, by extension, the mounting part 17 can be raised and lowered according to a height of the user U. The support 16 is not limited to the shape of a substantially quadrangular prism, and may have the shape of a substantially hexagonal prism or a support.

The mounting part 17 is a substantially rectangular plate-shaped table, and the ultrasound diagnostic apparatus 11 is attachably and detachably mounted on the mounting part 17. The mounting part 17 is inclined downward from the rear side to the front side to allow the user U to easily operate the ultrasound diagnostic apparatus 11. Further, a handle 21 is attached to the mounting part 17 to surround the mounting part 17. The handle 21 is gripped by the user U in a case where the user moves the cart 12. The handle 21 may be partially attached, for example, to a front or rear portion of the mounting part 17. Furthermore, the handle 21 may not be provided.

The ultrasound diagnostic apparatus 11 has a configuration similar to a laptop personal computer in which a display 25, an operation unit 26, a battery 27, a computer (not shown), and the like are integrated. The display 25 displays a menu screen, an ultrasound image display screen, and the like. The operation unit 26 includes a touch panel, a track-ball, various switches, and the like, and is operated by the user U. The display 25 and the operation unit 26 are connected to each other by a hinge, and can be opened to be used as shown in FIGS. 1, 2, and 3 or can be folded to be carried. An ultrasound probe (not shown) and the like are connected to the ultrasound diagnostic apparatus 11. "Computer" refers to a device in which a processor such as a central processing unit (CPU) or a field programmable gate array (FPGA), a memory for work of the processor, and a storage such as a hard disk are connected to each other via a busline.

The battery 27 is rechargeable and is built in the operation unit 26. The battery 27 supplies power to each part of the ultrasound diagnostic apparatus 11. The operating time of the ultrasound diagnostic apparatus 11 using the battery 27 is, for example, 1 hour to 2 hours.

The caster unit 15 includes the above-described casters 18, side beams 30, and a pedestal 31. The side beams 30 are two rods that extend in the front-rear direction, and two front and rear wheels, that is, casters 18 are attached to each side beam 30. The pedestal 31 is a substantially rectangular parallelepiped block that connects the two side beams 30. The pedestal 31 is disposed on a rear side of a center C1 (see also FIG. 4) of the caster unit 15 in the front-rear direction. Further, the lower end 19 of the support 16 is attached to the pedestal 31 such that the center of the lower end 19 coincides with a center C2 (see also FIG. 4) of the pedestal 31 in the front-rear direction and the left-right direction. For this reason, the support 16 is disposed on the rear side of the center C1 of the caster unit 15 in the front-rear direction. The center C1 is also a center of the caster unit 15 in the left-right direction.

A connector 32 (see FIG. 3) is provided in the pedestal 31. A battery unit 33 is electrically and mechanically connected to the connector 32. A rechargeable battery 34 (see FIG. 1), a power converter (not shown) that converts direct current power supplied from the battery 34 into alternating current power for a commercial power supply, and the like are built in the battery unit 33. The battery unit 33 supplies power of the battery 34 to the ultrasound diagnostic apparatus 11 mounted on the mounting part 17 via the connector 32. The battery unit 33 is for additional installation to compensate for the power shortage of the battery 27 of the ultrasound diagnostic apparatus 11. The operating time of the ultrasound diagnostic apparatus 11 using the battery unit 33 is, for example, 8 hours to 12 hours.

The battery unit 33 is disposed in front of the support 16 in a state in which the battery unit 33 is connected to the connector 32. More specifically, the battery unit 33 is disposed between the two side beams 30 in a state in which the battery unit 33 is connected to the connector 32. Much more specifically, the battery unit 33 is disposed between the two side beams 30 and the pedestal 31 in a state in which the battery unit 33 is connected to the connector 32. In other words, the battery unit 33 is disposed in a space 35 (see FIG. 4) that is surrounded on the front side of the support 16 by the two side beams 30 and the pedestal 31 in a state in which the battery unit 33 is connected to the connector 32.

As shown in FIGS. 2 and 3, each of the side beams 30 is provided with a holding mechanism 40 that holds the battery unit 33 to allow the battery unit 33 to be attachable and detachable. The holding mechanism 40 includes a guide rail 41 (see also FIG. 4). Flange parts 42 (see FIG. 3) attached to both left and right end portions of the battery unit 33 are placed on the guide rails 41. In a case where the battery unit 33 is to be attached, a cover 43 is detached from a front surface of the pedestal 31 and the flange parts 42 are then placed on the guide rails 41 with a small interval between the battery unit 33 and the pedestal 31 in the front-rear direction. Then, the battery unit 33 is slid from the front side to the rear side along the guide rails 41 until the battery unit 33 is connected to the connector 32. Finally, the guide rails 41 and the flange parts 42 are fastened to each other by several screws. The battery unit 33 is attached by a service man of a manufacturer of the ultrasound diagnostic system 10 in response to a request from the user U who has purchased the battery unit 33 for additional installation.

Figure 5:
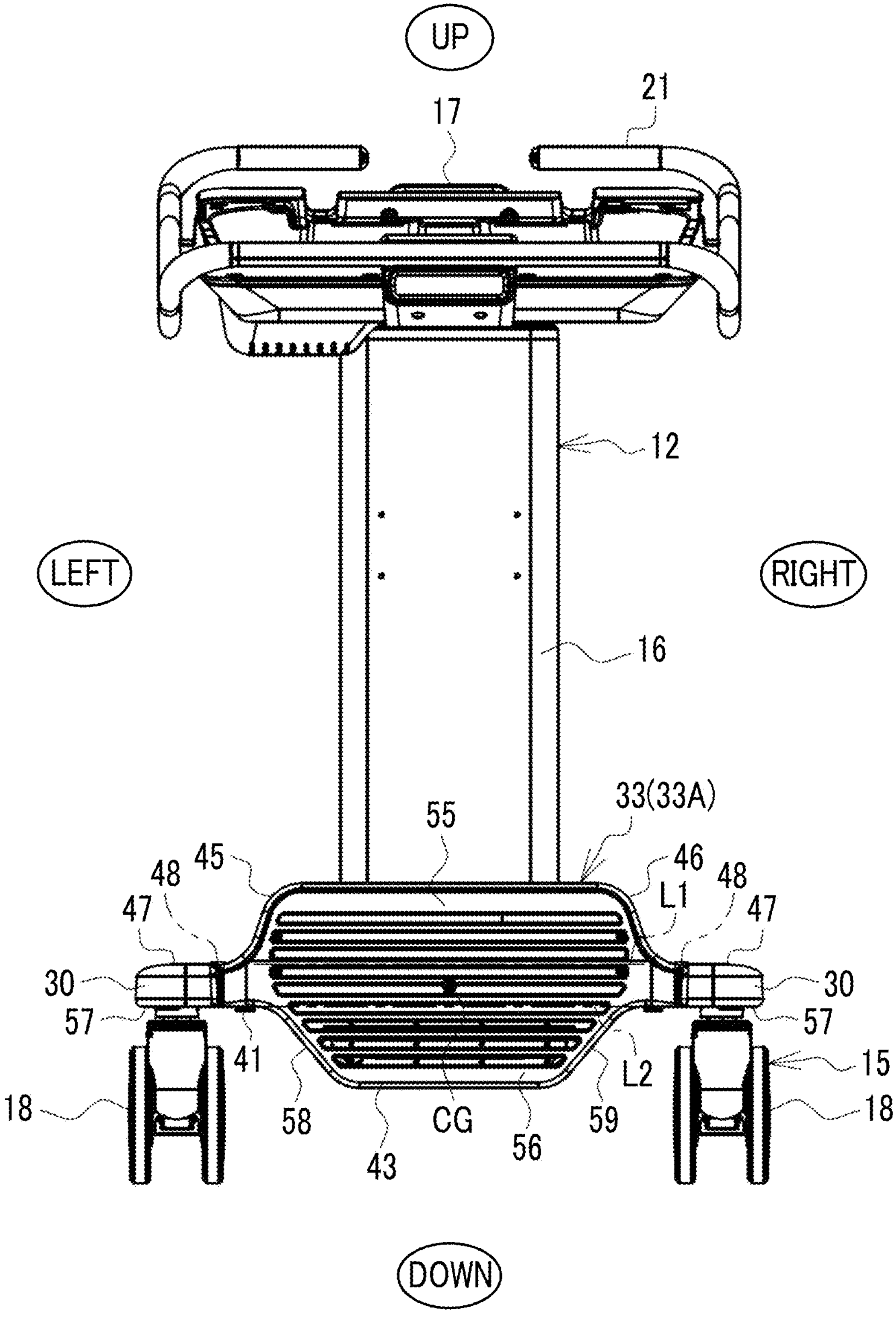
FIG. 5 is a front view of the cart for the ultrasound diagnostic apparatus.

The battery unit 33 has a curved surface shape having no corner on an outer peripheral surface as a whole as viewed from the front side (see FIG. 5). Further, as shown in FIG. 1, both left and right side surfaces 45 and 46 of the battery unit 33 and upper surfaces 47 of the side beams 30 on which the side surfaces 45 and 46 border form one smooth surface in a state in which the battery unit 33 is connected to the connector 32 (see also FIG. 5). In other words, the battery unit 33 and the side beams 30 are smoothly connected to each other by a continuous surface. In other words, there is no protruding portion at boundaries 48 between the side surfaces 45 and 46 of the battery unit 33 and the upper surfaces 47 of the side beams 30. However, a few gaps between members of the side beams 30 and the battery unit 33 may be formed at the boundaries 48. The side surfaces 45 and 46 are an example of an "outer peripheral surface of a battery unit" according to the technique of the present disclosure. Further, the upper surface 47 is an example of an "outer peripheral surface of a side beam" according to the technique of the present disclosure.

As shown in FIG. 2, the shape of the cross section of the pedestal 31 orthogonal to the front-rear direction is the same as that of the battery unit 33 orthogonal to the front-rear direction. A substantially hexagonal cross-sectional shape is exemplified as the shapes of the cross sections of the battery unit 33 and the pedestal 31 orthogonal to the front-rear direction. The term "the same" mentioned here refers to not only "completely the same" but also "the same" in the sense of including an error that is generally allowed in a technical field to which the technique of the present disclosure belongs and that does not contradict the gist of the technique of the present disclosure.

FIG. 1 shows a state in which the battery unit 33 is attached, and FIG. 2 shows a state in which the battery unit 33 is detached. FIG. 3 is an exploded perspective view of the ultrasound diagnostic system 10, that is, the ultrasound diagnostic apparatus 11, the cart 12, and the battery unit 33. In the state shown in FIG. 1, the ultrasound diagnostic apparatus 11 is operated by power supplied from the battery unit 33. In the state of FIG. 2, the ultrasound diagnostic apparatus 11 is operated by power supplied from its own battery 27. Further, the cover 43 is mounted on the front surface of the battery unit 33 in the state shown in FIG. 1, and the cover 43 is mounted on the front surface of the pedestal 31 in the state shown in FIG. 2. That is, the cover 43 is used for both the battery unit 33 and the pedestal 31. The cover 43 is provided with an indicator that notifies the user U of the remaining power of the battery 34 in a state shown in FIG. 1 in which the battery unit 33 is attached.

Figure 4:
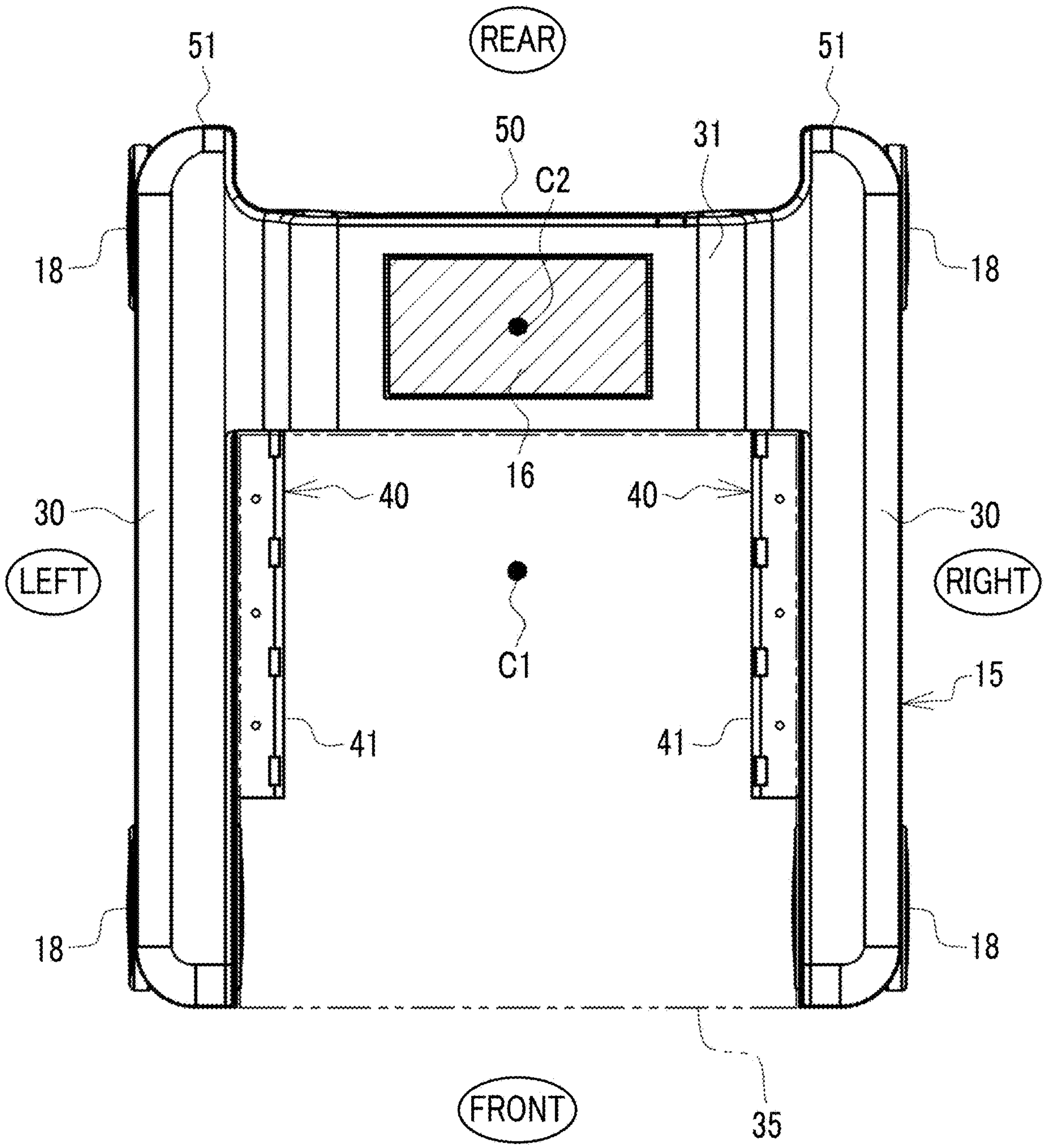
FIG. 4 is a plan view of a caster unit.

For example, as shown in FIG. 4, a rear end portion 50 of the pedestal 31 is positioned in front of rear end portions 51 of the side beams 30. For this reason, strictly, the caster unit 15 does not have a U shape and has an H shape in which a horizontal bar is significantly shifted to one side. Further, the pedestal 31 and, by extension, the support 16 are positioned in front of the two rear wheels, that is, casters 18.

For example, as shown in FIG. 5, the battery unit 33 protrudes above and below the side beams 30 as viewed from the front side in a state in which the battery unit 33 is connected to the connector 32. Widths (heights) of a portion 55 of the battery unit 33 that protrudes above the side beams 30 and a portion 56 (hereinafter, referred to as a lower portion) of the battery unit 33 that protrudes below the side beams 30 in the up-down direction are substantially the same.

A centroid CG of the battery unit is positioned at a level equal to or lower than the upper surface 47 of the side beam 30 in the up-down direction as viewed from the front side in a state in which the battery unit 33 is connected to the connector 32. Further, the centroid CG of the battery unit 33 is positioned between the upper surface 47 and a lower surface 57 of the side beam 30 in the up-down direction as viewed from the front side in a state in which the battery unit 33 is connected to the connector 32. Reference numeral L1 denotes a line that coincides with the upper surface 47 of the side beam 30, and reference numeral L2 denotes a line that coincides with the lower surface 57 of the side beam 30.

Both left and right side surfaces 58 and 59 of the lower portion 56 face the casters 18. Further, the side surfaces 58 and 59 are inclined toward sides opposite to the casters 18 as viewed from the front side. In other words, the lower portion 56 has a tapered shape downward as viewed from the front.

Figure 6:
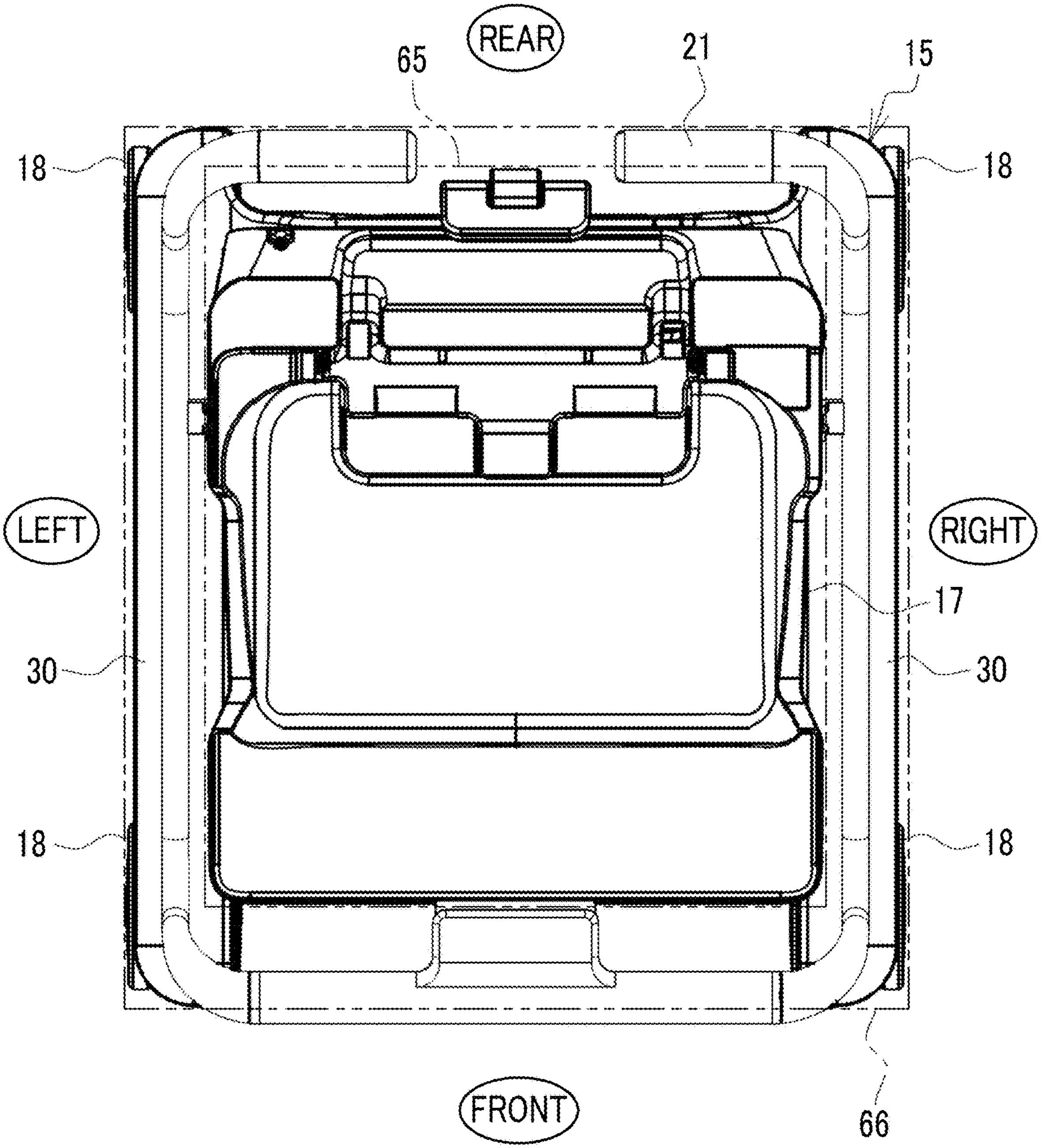
FIG. 6 is a plan view of the cart for the ultrasound diagnostic apparatus.

In FIG. 6 in which the cart 12 is viewed from above, a contour 65 of the mounting part 17 is positioned within a contour 66 of the caster unit 15. Here, the contour 65 of the mounting part 17 is a rectangle that surrounds an outermost contour of the substantially rectangular plate-shaped table forming the mounting part 17 excluding the handle 21. Further, the contour 66 of the caster unit 15 is a rectangle that surrounds an outermost contour of the casters 18 and the side beams 30.

Figure 7:
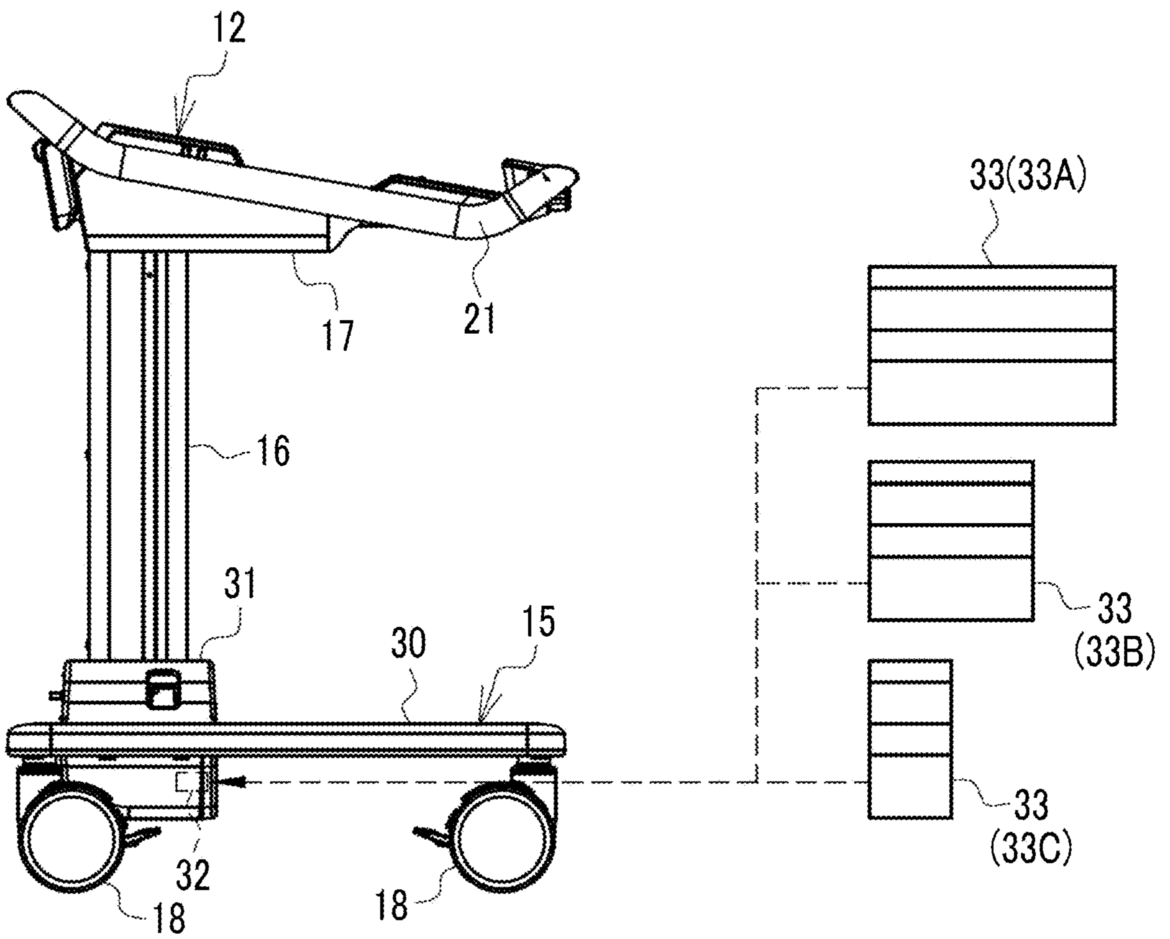
FIG. 7 is a diagram showing that a plurality of types of battery units can be connected to a connector.

For example, as shown in FIG. 7, three types of battery units 33A, 33B, and 33C can be connected to the connector 32. The battery unit 33A is the battery unit 33 shown in FIG. 1 and the like, and has the largest capacity and size of the battery 34 among the battery units 33A to 33C. The battery unit 33B has a capacity and a size of the battery 34 that are smaller than those of the battery unit 33A and are larger than those of the battery unit 33C. The battery unit 33C has the smallest capacity and size of the battery 34 among the battery units 33A to 33C.

As described above, the cart 12 comprises the caster unit 15, the support 16, the mounting part 17, and the connector 32. The caster unit 15 includes a total of four wheels, that is, casters 18 provided on the front, rear, left, and right sides. The lower end 19 of the support 16 is attached to the caster unit 15 and the support 16 extends upward. The support 16 is disposed on the rear side of the center C1 of the caster unit 15 in the front-rear direction. The mounting part 17 is attached to the upper end 20 of the support 16, and the ultrasound diagnostic apparatus 11 is mounted on the mounting part 17. The battery unit 33 that supplies power to the ultrasound diagnostic apparatus 11 and that is disposed in front of the support 16 is connected to the connector 32.

Since the support 16 is disposed on the rear side of the center C1 of the caster unit 15 in the front-rear direction, it is possible to reduce a risk that legs of the user U may bump into the support 16 during work. Further, since the battery unit 33 is disposed in front of the support 16, the attachment position of the support 16 is offset to the rear side of the center C1. As a result, the collapse of weight balance can be corrected. Therefore, according to the cart 12, it is easy to ensure weight balance and it is possible to improve the workability of the user U.

As shown in FIG. 1 and the like, the caster unit 15 includes the two side beams 30 to which the front and rear casters 18 are attached and which extend in the front-rear direction. Further, in a state in which the battery unit 33 is connected to the connector 32, the battery unit 33 is disposed between the two side beams 30. Since the battery unit 33 is disposed between the two side beams 30, the centroid of the cart 12 is positioned lower. As a result, weight balance can be further stabilized. Furthermore, since the battery unit 33 is sandwiched between the two side beams 30, the battery unit 33 can be protected from the legs of the user U, the wall of the medical facility, and the like.

As shown in FIG. 2 and the like, each of the side beams 30 is provided with the holding mechanism 40 that holds the battery unit 33 to allow the battery unit 33 to be attachable and detachable. Since not only a function to hold the casters 18 but also a function to hold the battery unit 33 is given to the side beams 30, a compact configuration can be achieved.

As shown in FIG. 2 and the like, the holding mechanism 40 includes the guide rail 41 that guides the battery unit 33, which is to be slid from the front side, toward the connector 32. For this reason, workability in a case where the battery unit 33 is to be attached can be improved.

In a state in which the battery unit 33 is connected to the connector 32 as shown in FIG. 1 and the like, the side surfaces 45 and 46 of the battery unit 33 and the upper surfaces 47 of the side beams 30 on which the side surfaces 45 and 46 border form one smooth surface. For this reason, in a case where the battery unit 33 is attached, a clean appearance can be obtained. As a result, design properties of the cart 12 can be enhanced. Further, since there is no snagging in a case where dirt such as dust adhering to the boundaries 48 between the side surfaces 45 and 46 and the upper surfaces 47 is to be wiped off with a sheet, cleaning can be easily performed.

As shown in FIG. 1 and the like, the caster unit 15 further includes the pedestal 31 that connects the two side beams 30. The pedestal 31 is disposed on the rear side of the center C1 of the caster unit 15 in the front-rear direction, and the lower end 19 of the support 16 is attached to the pedestal 31. For this reason, the support 16 can be stably held.

As shown in FIG. 3, the pedestal 31 is provided with the connector 32. Further, in a state in which the battery unit 33 is connected to the connector 32 as shown in FIG. 1 and the like, the battery unit 33 is disposed between the two side beams 30 and the pedestal 31. Since the battery unit 33 is disposed between the two side beams 30 and the pedestal 31, the centroid of the cart 12 is positioned lower. As a result, weight balance can be further stabilized. Furthermore, since the battery unit 33 is surrounded by the two side beams 30 and the pedestal 31, the battery unit 33 can be protected from the legs of the user U, the wall of the medical facility, and the like.

As shown in FIG. 4, the rear end portion 50 of the pedestal 31 is positioned in front of the rear end portions 51 of the side beams 30. For this reason, weight balance can be stabilized as compared to a case where the rear end portion 50 of the pedestal 31 and the rear end portions 51 of the side beams 30 are positioned at the same position and the centroid of the cart 12 is further shifted to the rear side.

As shown in FIG. 2, the shapes of the cross sections of the battery unit 33 and the pedestal 31 orthogonal to the front-rear direction are the same. For this reason, in a case where the battery unit 33 is attached, an appearance having unity can be obtained. As a result, design properties of the cart 12 can be enhanced. Further, since the attachment position of the battery unit 33 can be suggested to a service man through the shape of the pedestal 31, the service man can attach the battery unit 33 without hesitation. Furthermore, since a component such as the cover 43 can be used for both the pedestal 31 and the battery unit 33, the number of components can be reduced.

As shown in FIG. 5, the battery unit 33 protrudes above and below the side beams 30 as viewed from the front side in a state in which the battery unit 33 is connected to the connector 32. For this reason, since an upper space can be secured as compared to a case where the entire battery unit 33 protrudes above the side beams 30, for example, a tray for a treatment tool or the like can be attached in the secured upper space. Further, frequency with which the battery unit 33 rubs against a protrusion or the like of a floor surface can be reduced as compared to a case where the entire battery units 33 protrudes below the side beams 30.

As shown in FIG. 5, the centroid CG of the battery unit 33 is positioned at a level equal to or lower than the upper surface 47 of the side beam 30 in the up-down direction as viewed from the front side in a state in which the battery unit 33 is connected to the connector 32. Furthermore, the centroid CG of the battery unit 33 is positioned between the upper surface 47 and the lower surface 57 of the side beam 30 in the up-down direction. For this reason, weight balance can be further stabilized.

In addition, as shown in FIG. 5, the left and right side surfaces 58 and 59 of the lower portion 56 of the battery unit 33 are inclined toward sides opposite to the casters 18 as viewed from the front side. For this reason, it is possible to reduce a risk that the casters 18 may collide with the lower portion 56 and hinder the movement of the cart 12.

As shown in FIG. 6, the contour 65 of the mounting part 17 is positioned within the contour 66 of the caster unit 15 as viewed from above. For this reason, weight balance can be stabilized regardless of whether or not the battery unit 33 is attached, as compared to a case where the contour 65 of the mounting part 17 is not positioned within the contour 66 of the caster unit 15.

The battery unit 33 is for additional installation. For this reason, the operating time of the ultrasound diagnostic apparatus 11 can be increased as compared to a case where only the built-in battery 27 is used.

As shown in FIG. 7, a plurality of types of the battery units 33 having different capacities and sizes can be connected to the connector 32. For this reason, it is possible to select and use the battery unit 33 of a type that corresponds to a request of the user U. The battery unit 33 may not be for additional installation and may be provided as an accessory at the time of purchasing the cart 12.

The medical apparatus is the ultrasound diagnostic apparatus 11. Since the ultrasound diagnostic apparatus 11 is heavier than other medical apparatuses such as a sphygmomanometer and an electrocardiogramecessity of ensuring the weight balance of the ultrasound diagnostic apparatus 11 is higher than that of other medical apparatuses. Therefore, it is possible to greatly exhibit an effect of easily ensuring weight balance.

The medical apparatus is not limited to the exemplified ultrasound diagnostic apparatus 11. The medical apparatus may be a sphygmomanometer, an electrocardiograph, or the like described above, or may be, for example, a radiation generator, a processor of an electronic endoscope, or the like.

The casters 18 are not limited to the four wheels having been exemplified. The casters 18 may be a total of six wheels arranged such that one wheel is disposed between the two front and rear wheels. Further, three wheels may be provided such that one wheel is provided in the middle on the front side and two wheels are provided at the left and right on the rear side or, contrariwise, two wheels are provided at the left and right on the front side and one wheel is provided in the middle on the rear side.

In order to reduce the weight of the mounting part 17 provided on the upper side and stabilize weight balance, grooves, slits, and/or holes may be formed in the mounting part 17.

The holding mechanism that holds the battery unit 33 to allow the battery unit 33 to be attachable and detachable is not limited to the exemplified holding mechanism 40 including the guide rail 41. For example, the holding mechanism may be formed of grooves that are formed on both left and right side surfaces of the side beam 30 and are parallel to the front-rear direction, and protrusions that are formed on both left and right side portions of the battery unit 33 and are to be fitted into the grooves formed on both the left and right side surfaces of the side beam 30.

The connector 32 may be provided not on the pedestal 31 but the side beam 30.

Further, the caster unit 15 may have a U shape in which the rear end portion 50 of the pedestal 31 and the rear end portions 51 of the side beams 30 are positioned at the same position.

The number of types of the battery units 33 is not limited to three exemplified. The number of types of the battery units 33 may be two or four or more.

From the above description, it is possible to understand techniques described in the following supplementary aspects.

Supplementary Aspect 1

A cart for a medical apparatus comprising:

a caster unit that includes a plurality of casters provided on front, rear, left, and right sides;

a support of which a lower end is attached to the caster unit and which extends upward and is disposed on a rear side of a center of the caster unit in a front-rear direction;

a mounting part which is attached to an upper end of the support and on which a medical apparatus is mounted; and a connector to which a battery unit that supplies power to the medical apparatus and is disposed in front of the support is connected.

Supplementary Aspect 2

The cart for a medical apparatus according to supplementary aspect 1, wherein the caster unit includes two side beams to which the front and rear casters are attached and which extend in the front-rear direction, and the battery unit is disposed between the two side beams in a state in which the battery unit is connected to the connector.

Supplementary Aspect 3

The cart for a medical apparatus according to supplementary aspect 2, wherein the side beam is provided with a holding mechanism that holds the battery unit to allow the battery unit to be attachable and detachable.

Supplementary Aspect 4

The cart for a medical apparatus according to supplementary aspect 3, wherein the holding mechanism includes a guide rail that guides the battery unit, which is to be slid from a front side, toward the connector.

Supplementary Aspect 5

The cart for a medical apparatus according to any one of supplementary aspects 2 to 4, wherein in a state in which the battery unit is connected to the connector, an outer peripheral surface of the battery unit and outer peripheral surfaces of the side beams on which the outer peripheral surface of the battery unit borders form one smooth surface.

Supplementary Aspect 6

The cart for a medical apparatus according to any one of supplementary aspects 2 to 5, wherein the caster unit further includes a pedestal that connects the two side beams, the pedestal is disposed on a rear side of a center of the caster unit in the front-rear direction, and a lower end of the support is attached to the pedestal.

Supplementary Aspect 7

The cart for a medical apparatus according to supplementary aspect 6, wherein the pedestal is provided with the connector, and the battery unit is disposed between the two side beams and the pedestal in a state in which the battery unit is connected to the connector.

Supplementary Aspect 8

The cart for a medical apparatus according to supplementary aspect 6 or 7, wherein a rear end portion of the pedestal is positioned in front of rear end portions of the side beams.

Supplementary Aspect 9

The cart for a medical apparatus according to any one of supplementary aspects 6 to 8, wherein shapes of cross sections of the battery unit and the pedestal orthogonal to the front-rear direction are the same.

Supplementary Aspect 10

The cart for a medical apparatus according to any one of supplementary aspects 2 to 9, wherein the battery unit protrudes above and below the side beams as viewed from a front side in a state in which the battery unit is connected to the connector.

Supplementary Aspect 11

The cart for a medical apparatus according to supplementary aspect 10, wherein a centroid of the battery unit is positioned at a level equal to or lower than an upper surface of the side beam in an up-down direction as viewed from the front side in a state in which the battery unit is connected to the connector.

Supplementary Aspect 12

The cart for a medical apparatus according to supplementary aspect 10 or 11, wherein a centroid of the battery unit is positioned between an upper surface and a lower surface of the side beam in an up-down direction as viewed from the front side in a state in which the battery unit is connected to the connector.

Supplementary Aspect 13

The cart for a medical apparatus according to any one of supplementary aspects 10 to 12, wherein both left and right side surfaces of a portion of the battery unit, which protrudes below the side beams in a state in which the battery unit is connected to the connector, are inclined toward sides opposite to the casters as viewed from the front side.

Supplementary Aspect 14

The cart for a medical apparatus according to any one of supplementary aspects 1 to 13, wherein a contour of the mounting part is positioned within a contour of the caster unit as viewed from above.

Supplementary Aspect 15

The cart for a medical apparatus according to any one of supplementary aspects 1 to 14, wherein the battery unit is for additional installation.

Supplementary Aspect 16

The cart for a medical apparatus according to any one of supplementary aspects 1 to 15, wherein a plurality of types of the battery units having different capacities and sizes are capable of being connected to the connector.

Supplementary Aspect 17

The cart for a medical apparatus according to any one of supplementary aspects 1 to 16, wherein the medical apparatus is an ultrasound diagnostic apparatus.

Various embodiments and/or various modification examples described above can also be appropriately combined in the technique of the present disclosure. Further, it is natural that the present disclosure is not limited to each embodiment described above and may employ various configurations without departing from the scope.

The above-described contents and illustrated contents are detailed descriptions for parts according to the disclosed technique and are merely an example of the disclosed technique. For example, the description of the configuration, functions, actions, and effects having been described above is the description of examples of the configuration, functions, actions, and effects of the portions according to the technique of the present disclosure. Accordingly, it goes without saying that unnecessary portions may be deleted or new elements may be added or replaced in the description contents and shown contents described above without departing from the scope of the technique of the present disclosure. In addition, particularly, description related to common technical knowledge or the like that does not need to be described in terms of embodying the disclosed technique is omitted in the above-described contents and the illustrated contents in order to avoid complication and to facilitate understanding of the parts according to the disclosed technique.

In this specification, “A and/or B” is synonymous with “at least one of A or B”. That is, “A and/or B” may mean only A, may mean only B, or may mean a combination of A and B. In addition, in this specification, the same approach as “A and/or B” is applied to a case where three or more matters are represented by connecting the matters with “and/or”.

All documents, patent applications, and technical standards described in this specification are incorporated in this specification by reference to the same extent as in a case where each of the documents, the patent applications, and the technical standards are specifically and individually indicated to be incorporated by reference.

What is claimed is:

1. A cart for a medical apparatus comprising:

a caster unit that includes a plurality of casters provided on front, rear, left, and right sides;

a support of which a lower end is attached to the caster unit and which extends upward and is disposed on a rear side of a center of the caster unit in a front-rear direction;

a mounting part which is attached to an upper end of the support and on which a medical apparatus is mounted; and a connector to which a battery unit that supplies power to the medical apparatus and is disposed in front of the support is connected;

wherein the caster unit includes two side beams to which the front and rear casters are attached and which extend in the front-rear direction, and the battery unit is disposed between the two side beams in a state in which the battery unit is connected to the connector;

wherein the battery unit protrudes above and below the side beams as viewed from a front side in a state in which the battery unit is connected to the connector;

wherein a centroid of the battery unit is positioned at a level equal to or lower than an upper surface of the side beam in an up-down direction as viewed from the front side in a state in which the battery unit is connected to the connector.

2. The cart for a medical apparatus according to claim 1, wherein the side beam is provided with a holding mechanism that holds the battery unit to allow the battery unit to be attachable and detachable.

3. The cart for a medical apparatus according to claim 2, wherein the holding mechanism includes a guide rail that guides the battery unit, which is to be slid from a front side, toward the connector.

4. The cart for a medical apparatus according to claim 1, wherein in a state in which the battery unit is connected to the connector, an outer peripheral surface of the battery unit and outer peripheral surfaces of the side beams on which the outer peripheral surface of the battery unit borders form one smooth surface.

5. The cart for a medical apparatus according to claim 1, wherein the caster unit further includes a pedestal that connects the two side beams, the pedestal is disposed on a rear side of a center of the caster unit in the front-rear direction, and a lower end of the support is attached to the pedestal.

6. The cart for a medical apparatus according to claim 5, wherein the pedestal is provided with the connector, and the battery unit is disposed between the two side beams and the pedestal in a state in which the battery unit is connected to the connector.

7. The cart for a medical apparatus according to claim 5, wherein a rear end portion of the pedestal is positioned in front of rear end portions of the side beams.

8. The cart for a medical apparatus according to claim 5, wherein shapes of cross sections of the battery unit and the pedestal orthogonal to the front-rear direction are the same.

9. The cart for a medical apparatus according to claim 1, wherein a centroid of the battery unit is positioned between an upper surface and a lower surface of the side beam in an up-down direction as viewed from the front side in a state in which the battery unit is connected to the connector.

10. The cart for a medical apparatus according to claim 1, wherein both left and right side surfaces of a portion of the battery unit, which protrudes below the side beams in a state in which the battery unit is connected to the connector, are inclined toward sides opposite to the casters as viewed from the front side.

11. The cart for a medical apparatus according to claim 1, wherein a contour of the mounting part is positioned within a contour of the caster unit as viewed from above.

12. The cart for a medical apparatus according to claim 1, wherein the battery unit is for additional installation.

13. The cart for a medical apparatus according to claim 1, wherein a plurality of types of the battery units having different capacities and sizes are capable of being connected to the connector.

14. The cart for a medical apparatus according to claim 1, wherein the medical apparatus is an ultrasound diagnostic apparatus.

* * * * *